(12) United States Patent
Oftring et al.

(10) Patent No.: US 7,880,035 B2
(45) Date of Patent: Feb. 1, 2011

(54) METHOD FOR PRODUCING ETHYLENEAMINES

(75) Inventors: Alfred Oftring, Bad Dürkheim (DE); Kirsten Dahmen, Freinsheim (DE); Thilo Hahn, Kirchheimbolanden (DE); Randolf Hugo, Dirmstein (DE); Katrin Baumann, Mannheim (DE); Johann-Peter Melder, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/529,079

(22) PCT Filed: Feb. 28, 2008

(86) PCT No.: PCT/EP2008/052414

§ 371 (c)(1),
(2), (4) Date: Aug. 28, 2009

(87) PCT Pub. No.: WO2008/104583

PCT Pub. Date: Sep. 4, 2008

(65) Prior Publication Data

US 2010/0056828 A1    Mar. 4, 2010

(30) Foreign Application Priority Data

Mar. 1, 2007    (EP) .................................. 07103293

(51) Int. Cl.
*C07C 209/48* (2006.01)
(52) U.S. Cl. ........................................ 564/490; 564/491
(58) Field of Classification Search .................. None
See application file for complete search history.

(56) References Cited

U.S. PATENT DOCUMENTS 3,255,248 A  6/1966  Suessenguth et al.
4,235,821 A  11/1980  Butte, Jr. et al.
5,530,127 A  6/1996  Reif et al.
6,469,211 B2  10/2002  Ansmann et al.
6,518,449 B1  2/2003  Boschat et al.

FOREIGN PATENT DOCUMENTS

| DE | 1154121 | | 9/1963 |
| DE | 3003729 | A1 | 8/1980 |
| EP | 0212986 | A1 | 3/1987 |
| EP | 0382508 | A2 | 8/1990 |
| EP | 0696572 | A1 | 2/1996 |
| EP | 0963975 | A1 | 12/1999 |
| EP | 1209146 | A1 | 5/2002 |
| EP | 1742045 | A1 | 1/2007 |
| WO | WO-9933561 | A1 | 7/1999 |

OTHER PUBLICATIONS

U.S. Appl. No. 12/529,101, filed Aug. 28, 2009.
U.S. Appl. No. 12/529,096, filed Aug. 28, 2009.
U.S. Appl. No. 12/529,034, filed Aug. 28, 2009.
U.S. Appl. No. 12/529,047, filed Aug. 28, 2009.
U.S. Appl. No. 12/529,072, filed Aug. 28, 2009.
U.S. Appl. No. 12/529,087, filed Aug. 28, 2009.
U.S. Appl. No. 12/529,107, filed Aug. 28, 2009.
Nishimura, Shigeo, "Handbook of Heterogeneous Catalytic Hydrogenation for Organic Synthesis", (2001) pp. 213-215.
Malveda, Michael P., "CEH Product Review: Ethyleneamines"; SRI Report, SRI International, (2003), pp. 1-53.
Gamage, Swarna A., et al., "Dicationic Bis(9-methylphenazine-1-carboxamides): Relationships between Biological Activity and Linker Chain Structure for a Series of Potent Topoisomerase Targeted Anticancer Drugs", J. Med., Chem, (2001), vol. 44, pp. 1407-1415.

*Primary Examiner*—Brian J Davis
(74) *Attorney, Agent, or Firm*—Connolly Bove Lodge & Hutz LLP

(57) ABSTRACT

The invention relates to a process for preparing an ethylene amine mixture, which comprises hydrogenating an amino nitrile mixture comprising at least 30% by weight of aminoacetonitrile (AAN) and at least 5% by weight of iminodiacetonitrile (IDAN) in the presence of a catalyst. Ethylenediamine (EDA) and/or diethylenetriamine (DETA) and, if appropriate, further ethylene amines can be isolated from the ethylene amine mixtures obtained.

14 Claims, No Drawings

METHOD FOR PRODUCING ETHYLENEAMINES

CROSS-REFERENCE TO RELATED APPLICATIONS

This application is a national stage application (under 35 U.S.C. §371) of PCT/EP2008/052414, filed Feb. 28, 2008, which claims benefit of European application 07103293.2, filed Mar. 1, 2007.

BACKGROUND OF THE INVENTION

The invention relates to a process for preparing an ethylene amine mixture by hydrogenation of an amino nitrite mixture over a catalyst. The individual ethylene amines can, if appropriate, be isolated from the ethylene amine mixture obtained.

It is generally known that nitrites can be hydrogenated in the presence of catalysts to give the corresponding amines. Depending on the reaction parameters chosen, the known processes give the desired products, for example primary amines as main product and secondary and tertiary amines as by-products. A problem here is often that the desired product is obtained with lower selectivity and/or in lower yield, frequently also accompanied by rapid deactivation of the catalyst used.

In addition, it is known that in processes for preparing amines by hydrogenation of nitrites a certain proportion of ammonia improves the selectivity of the hydrogenation to primary amines and suppresses the formation of secondary and tertiary amines. However, hydrogenation in the presence of ammonia involves an additional engineering outlay associated with separation of the ammonia from the product stream, the work-up and possible recirculation of the ammonia. In addition, higher pressures can be required in the hydrogenation, since the partial pressure of the ammonia has to be taken into account.

Thus, ethylenediamine (EDA), which is a starting material for, for example, the synthesis of complexing agents or bleach activators which are used, inter alia, as additives for laundry detergents or cleaners, can be prepared as main product by hydrogenation of aminoacetonitrile (MN). The hydrogenation of iminodiacetonitrile (IDAN) analogously gives diethylenetriamine (DETA) as main product. However, the hydrogenation of MN or IDAN also always gives DETA or EDA, respectively, as by-products. Depending on the reaction conditions selected, further amine compounds can also be obtained as by-products.

DE-A 3 003 729 describes a process for the hydrogenation of aliphatic nitrites, alkylene oxy nitrites and alkylene amino nitrites to primary amines over a cobalt or ruthenium catalyst in the presence of a solvent system. The solvent system used comprises water and ammonia together with an ether or polyether which preferably has from 4 to 6 carbon atoms and a carbon to oxygen ratio of from 2:1 to 5:1, e.g. dioxane, tetrahydrofuran, methylene glycol dimethyl ether or diethylene glycol dimethyl ether, with cyclic ethers such as dioxane and tetrahydrofuran being particularly preferred. As nitrile component, particular preference is given to dinitriles. However, DE-A 3003 729 does not disclose that compounds having both a cyano group and an amino group, e.g. AAN, can also be used in the process.

EP-A 0 382 508 describes a process for the batchwise preparation of acyclic, aliphatic polyamines by hydrogenation of acyclic, aliphatic polynitriles in the liquid phase over Raney cobalt catalysts, preferably in the presence of anhydrous ammonia. Here, a polynitrile solution is fed into a reaction zone which comprises the Raney cobalt catalyst in an essentially oxygen-free atmosphere. During the entire reaction time, the polynitrile solution is fed in at a rate which is not greater than the maximum rate at which the polynitrile reacts with the hydrogen in the reaction zone. A reaction parameter K which is suitable for determining the volume feed rate is also mentioned. The process described is restricted to the preparation of polyamines from polynitriles such as iminodiacetonitrile (IDAN), nitrilotriacetonitrile or further compounds having 2 or more cyano groups. However, the reaction of compounds having one cyano group, e.g. MN to EDA, is not described.

EP-A 212 986 relates to a further process in which aliphatic polynitriles can be hydrogenated over a granular Raney cobalt catalyst in the presence of a liquid primary or secondary amine comprised in the feed stream to give the corresponding polyamines. Mention is made of, inter alia, the amino component EDA which always has to be present and also numerous further primary or secondary amines. Furthermore, this document specifically discloses that IDAN can be hydrogenated to DETA.

DE-A 1 154 121 relates to a process for preparing ethylenediamine in which the starting materials hydrocyanic acid, formaldehyde, ammonia and hydrogen are reacted in the presence of a catalyst in a one-pot process. Both the ammonia and the hydrogen are used in a molar excess over the further starting materials hydrocyanic acid and formaldehyde which are present in equimolar amounts. In this process, the MN formed in situ is thus not isolated but directly reacted further with hydrogen. A disadvantage of this process is that the desired product (EDA) is obtained relatively unselectively in small amounts.

U.S. Pat. No. 3,255,248 describes a process for the hydrogenation of organic nitrogen-carbon compounds, which preferably have amino groups substituted by nitro, N-nitroso, isonitroso or cyano groups or by aromatics, to the corresponding amines in the liquid phase using a sintered catalyst comprising cobalt or nickel. Here, the starting material is sprinkled either alone or in the presence of a solvent, for example water, tetrahydrofuran, methanol, ammonia or the reaction product formed, together with the hydrogen onto the catalyst. If compounds which are unsaturated at the nitrogen atom, e.g. cyano groups, are hydrogenated, the presence of ammonia in the reaction is recommended. This is made clear in Example 1 of this patent, where aminoacetonitrile is sprinkled in the form of an aqueous solution together with liquid ammonia but without another solvent onto the sintered catalyst. The pressure used was 280 atm.

EP-A 1 209 146 relates to a further process for the continuous hydrogenation of nitrites to primary amines, in which the respective nitrites are used in the liquid phase over a suspended, activated Raney catalyst based on an alloy of aluminum and the reaction is carried out in the absence of ammonia and basic alkali metal or alkaline earth metal compounds. Among many others, AAN and IDAN can be used as nitrites in the reaction to form the corresponding ethylene amines. If appropriate, the nitrile to be hydrogenated can also be present in solution in an organic solvent, preferably an alcohol, amine, amide, in particular N-methylpyrrolidone (NMP) and dimethylformamide (DMF), or an ether or ester. However, EP-A 1 209 146 gives no indication that IDAN and AAN can be hydrogenated jointly.

Thus, none of the prior art reports that mixtures of amino nitrites which comprise IDAN and AAN can also be hydrogenated. Rather, the processes of the prior art are restricted to the hydrogenation of individual substances.

BRIEF SUMMARY OF THE INVENTION

It is accordingly an object of the present invention to provide a simple and inexpensive process for preparing the ethylene amines EDA and/or DETA and, if appropriate, further ethylene amines such as Pip by hydrogenation of the corresponding amino nitrites. A high conversion at high selectivity should be achieved in each case, with the ratio of DETA to EDA being variable.

This object is achieved by a process for preparing an ethylene amine mixture, which comprises hydrogenating an amino nitrite mixture comprising at least 30% by weight of aminoacetonitrile (MN) and at least 5% by weight of iminodiacetonitrile (IDAN) in the presence of a catalyst. For the purposes of the present invention, hydrogenation means reaction of the amino nitrile mixture with hydrogen.

DETAILED DESCRIPTION OF THE INVENTION

The process of the invention has the advantage that the main components of the ethylene amine mixture (EDA and DETA) can be prepared at a high conversion and/or with high selectivity (higher space time yield). The amino nitrile mixture used is preferably reacted completely or virtually completely. This is particularly important in industrial processes since unreacted starting material generally has to be recirculated to the process circuit or be disposed of. Processes in which large amounts of AAN and/or IDAN are not reacted are particularly disadvantageous because of the high instability of AAN and IDAN. Firstly, AAN and also IDAN tends to decompose at relatively high temperatures, so that the decomposition products cannot be recirculated to the respective circuit, and secondly this decomposition can also proceed with explosive vigor. Since the amino nitrile mixture can be reacted completely in the process of the invention, no efforts have to be made to recirculate it to the production cycle.

An advantage of the preparation of an ethylene amine mixture instead of the preparation of individual components in separate campaigns or in separate processes is that the addition of ammonia can be dispensed with. In the specific preparation of ethylene amines according to the prior art, ammonia or other additives are generally added to suppress secondary amines. In the synthesis according to the invention of ethylene amine mixtures, suppression of dimerization is not necessary since the dimers are obtained in the product mix and represent products of value. In contrast, in the case of separate syntheses, components obtained in small concentrations cause separation problems and therefore interfere, even if they are products of value. The avoidance of ammonia leads to savings in terms of apparatus as a result of the absence of ammonia separation, storage or recirculation and also possible lower pressures in the hydrogenation reactor due to the intrinsic pressure of ammonia no longer being present. For safety reasons, too, the avoidance of ammonia is advantageous.

Despite the fact that an ethylene amine mixture is obtained in principle in the process of the invention, the main components EDA, DETA and possibly also other ethylene amines obtained as by-products can be obtained by continuous isolation in a single plant. In conventional processes in which the amino nitrites are hydrogenated separately, DETA, EDA and/or further ethylene amines (in each case depending on the starting material used) are in principle always obtained as by-products. Accordingly, the same purification steps as in the process of the invention are generally necessary for separating off the by-products from the respective main product after the individual specific ethylene amine syntheses. Methods of separating off the by-products (DETA or EDA) obtained in the individual processes thus do not differ in principle from methods of isolating the main products (e.g. EDA and DETA) obtained in the process of the invention, only the amount of EDA or DETA to be separated off is different. In addition, in campaign operation, only batchwise operation comes into question, which is impractical because of the desired amounts. In the case of continuous operation, shutdowns and changing over of the plants have to be accepted (reduction in plant availability, cleaning requirements, losses of product, personnel requirements, etc.). Storage capacities corresponding to market requirements also have to be present.

Another advantage is that, depending on market requirements, a higher or lower proportion of EDA or DETA can be prepared. Thus, it is possible to use specific amino nitrile mixture compositions in the process of the invention in order to serve the quantity ratios desired on the market. The process of the invention gives an ethylene amine mixture comprising at least 30% of EDA together with at least 5% of DETA with high selectivity. Further ethylene amines which may be formed can also represent products of value and be isolated as such.

While AAN is a liquid at room temperature, IDAN is solid at room temperature (RT) and is not readily soluble in customary inert solvents. Owing to the good solubility of IDAN in AAN, the handling of solids can be avoided in the process of the invention. For example, a solution concentration of only ~10% of IDAN in THF is possible at room temperature, while solution concentrations of up to 35% in AAN are possible.

A further disadvantage of the separate preparation of DETA is the high degree to which it complexes the catalyst. The resulting product inhibition results in a relatively slow hydrogenation rate. In the preparation of EDA, the product inhibition is significantly lower, so that a considerably higher hydrogenation rate of AAN is possible, presumably because of lower complexation constants. If the hydrogenation is carried out in the presence of at least 30% by weight of MN as in the process of the invention, the product inhibition of the corresponding ethylene amines is reduced, with the total product inhibition being significantly lower or no longer discernible. For a given amino nitrile mixture, the space-time yield of the respective components is therefore greater than in the corresponding hydrogenation of the individual components, or the hydrogenation of the mixture can be carried out at significantly lower pressures, as a result of which significantly lower capital costs are made possible.

The process of the invention starts out from an amino nitrile mixture as starting material. The amino nitrile mixture comprises at least 30% by weight of aminoacetonitrile (MN) together with at least 5% by weight of iminodiacetonitrile (IDAN). If appropriate, further amino nitrites can be comprised. MN is normally comprised in an amount of from 30 to 95% by weight, preferably from 50% to 95% by weight, particularly preferably from 75% to 90% by weight, in the amino nitrile mixture. The amino nitrile mixture normally comprises from 5 to 70% by weight, preferably from 5 to 50% by weight, of IDAN. It particularly preferably comprises from 10 to 25% by weight of IDAN. The above percentages by weight of MN and IDAN are based on the total amount of amino nitrites comprised in the mixture. Any water or solvent present are not taken into account in these amounts.

It is generally possible to use any type/grade of AAN or IDAN. If appropriate, the amino nitrites can also be used in the form of their aqueous or aqueous ammoniacal solution. Processes for preparing MN or IDAN are known to those skilled in the art. AAN and/or IDAN are preferably prepared by reaction of $NH_3$ and formaldehyde cyanohydrin (FACH).

IDAN and AAN can be synthesized separately and combined in the appropriate amounts to form the amino nitrile mixture before use in the process of the invention. AAN and IDAN can also be prepared together if appropriate; the amino nitrile mixture comprising at least 30% by weight of MN and at least 5% by weight of IDAN can subsequently be produced by appropriate enrichment and/or depletion in IDAN or AAN.

The two main components of the amino nitrile mixture are, as indicated above, AAN and IDAN. IDAN is a solid at room temperature, while MN is a liquid, with IDAN being largely soluble in AAN. In the process of the invention, the amino nitrile mixture itself is preferably subjected to hydrogenation as a liquid (solution). Since the amino nitrile mixture can be fed to the hydrogenation as a liquid under the reaction conditions employed in the process of the invention, it is not absolutely necessary for the hydrogenation of the amino nitrile mixture to be carried out in the presence of a further solvent, e.g. an organic solvent and/or water. However, the additional use of an organic solvent (inert organic compound) and/or of water is found to be advantageous since stabilization of the individual components of the amino nitrile mixture, in particular in the presence of the resulting amines, can be achieved by, in particular, the use of an organic solvent. In addition, a rinsing effect on the catalyst used can be achieved by the use of solvents, as a result of which its operating life can be increased or its consumption decreased and the space velocity of the catalyst can be improved.

A suitable solvent which can comprise one or more components should preferably have the following properties:
(a) the solvent should have a stabilizing effect on components of the amino nitrile mixture, in particular reduce decomposition of MN or IDAN at the prevailing temperatures;
(b) the solvent should have a good dissolution capability for hydrogen;
(c) the solvent should be inert under the reaction conditions;
(d) the reaction mixture (amino nitrile mixture; if appropriate water and solvent) should form a single phase under the reaction conditions;
(e) the solvent should be selected with a view to a preferred separation of the product from the product stream by distillation after the hydrogenation so as to avoid separations which require a large amount of energy or are complicated in terms of apparatus (e.g. close-boiling mixtures or azeotropes which are difficult to separate);
(f) the solvent should be able to be separated readily from the products, i.e. the boiling point should be sufficiently different from that of the products. Here, a boiling point lower than that of the products is preferred.

Possible solvents are organic solvents, for example amides such as N-methylpyrrolidone (NMP) and dimethylformamide (DMF), aromatic and aliphatic hydrocarbons such as benzene and xylene, alcohols such as methanol, ethanol, propanol, isopropanol, butanol, isobutanol, secondary butanol and tertiary butanol, amines such as alkylamines, ethylene amines, esters such as methyl acetate or ethyl acetate and ethers such as diisopropyl ether, diisobutyl ether, glycol dimethyl ether, diglycol dimethyl ether, dioxane and tetrahydrofuran (THF). Ethers are preferably used in the process of the invention, more preferably cyclic ethers and particularly preferably tetrahydrofuran. In a further preferred embodiment, alcohols, in particular methanol, are used as organic solvent.

The solvent is used in a weight ratio to the amino nitrile mixture used of from 0.1:1 to 15:1. The concentration of the amino nitrile mixture in the solution in which the hydrogenation is carried out should be selected so that a suitable feed rate or residence time can be set. Preference is given to mixing the amino nitrile mixture in an amount of from 10 to 50% by weight with the solvent. Based on the particularly preferred solvents methanol and tetrahydrofuran, it is advantageous, for example, to use the amino nitrile mixture in an amount of from 20 to 40% by weight based on the solvent.

The solution used for the preparation of ethylene amines by hydrogenation of the amino nitrile mixture can comprise a proportion of water in addition to the amino nitrile mixture and any solvent. The amino nitrile mixture is preferably hydrogenated directly; if appropriate, water can be separated off at least partly or in its entirety and the amino nitrile mixture can then be hydrogenated.

If appropriate, additional additives can be comprised in the solution in which the hydrogenation is carried out. Possible additives are principally hydroxides such as alkali metal hydroxides, alkoxides, amides or amines such as ammonia. Furthermore, acidic additives such as silicates can be additionally comprised in the solution. These substances can be added as pure substance or as a solution in a solvent. The process of the invention is preferably carried out without addition of additives.

In a preferred embodiment of the process, no ammonia is added to the solution in which the hydrogenation is carried out. If ammonia is present in dissolved form in the starting materials or in any aqueous solution used or is liberated as by-product in the hydrogenation, this does not interfere. Any ammonia present can be removed by methods known to those skilled in the art, for example by distillation.

As catalysts for the hydrogenation of the nitrite function to the amine, it is possible to use catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species. These include skeletal catalysts (also referred to as Raney® type; hereinafter also Raney catalyst) which are obtained by leaching (activation) of an alloy of hydrogenation-active metal and a further component (preferably Al). The catalysts can additionally comprise one or more promoters. In a preferred embodiment, Raney catalysts, preferably Raney cobalt or Raney nickel catalysts and particularly preferably Raney cobalt catalysts doped with at least one of the elements Cr, Ni or Fe or Raney nickel catalysts doped with one of the elements Mo, Cr or Fe, are used in the process of the invention.

The catalysts can be used as all-active catalysts or in supported form. Supports employed are preferably metal oxides such as $Al_2O_3$, $SiO_2$, $ZrO_2$, $TiO_2$, mixtures of metal oxides or carbon (activated carbons, carbon blacks, graphite).

The oxidic catalysts are activated by reduction of the metal oxides in a hydrogen-comprising gas stream at elevated temperature either outside the reactor or in the reactor before use. If the catalysts are reduced outside the reactor, this can be followed by passivation by means of an oxygen-comprising gas stream or embedding in an inert material in order to avoid uncontrolled oxidation in air and to make safe handling possible. As inert material, it is possible to use organic solvents such as alcohols or else water or an amine, preferably the reaction product. An exception in the activation is the skeletal catalysts which can be activated by leaching with aqueous base, as described in, for example, EP-A 1 209 146.

Depending on the process carried out (suspension hydrogenation, fluidized-bed process, fixed-bed hydrogenation), the catalysts are used as powder, crushed material or shaped bodies (preferably extrudates or pellets).

Particularly preferred fixed-bed catalysts are the all-active cobalt catalysts doped with Mn, P and alkali metal (Li, Na, K, Rb, Cs) which are disclosed in EP-A 742 045. The active catalyst composition of these catalysts before reduction with hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar Ni:Cu ratio being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst A disclosed in this document which has the composition 33% by weight of Zr, calculated as $ZrO_2$, 28% by weight of Ni, calculated as NiO, 11% by weight of Cu, calculated as CuO, and 28% by weight of Co, calculated as CoO.

Further suitable catalysts are those disclosed in EP-A 696 572, whose catalytically active composition before reduction with hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$; for example the catalyst specifically disclosed in this document which has the composition 31.5% by weight of $ZrO_2$, 50% by weight of NiO, 17% by weight of CuO and 1.5% by weight of $MoO_3$. Further suitable catalysts are those described in WO-A-99/44984, which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight based on (a) of a compound based on an alkali metal and/or alkaline earth metal and (d) from 0.001 to 1% by weight based on (a) manganese.

Suspension processes are preferably carried out using Raney catalysts. In the case of Raney catalysts, the active catalyst is produced as "metal sponge" from a binary alloy (nickel, iron, cobalt with aluminum or silicon) by leaching out of one component by means of acid or alkali. Residues of the original alloying component often have a synergistic action.

The Raney catalysts used in the process of the invention are preferably produced from an alloy of cobalt or nickel, particularly preferably cobalt, and a further alloying component which is soluble in alkalis. Aluminum is preferably used as this soluble alloying component, but it is also possible to use other components such as zinc and silicon or mixtures of such components.

To activate the Raney catalyst, the soluble alloying component is completely or partly extracted with alkali, for which purpose it is possible to use, for example, aqueous sodium hydroxide. The catalyst can then be washed with, for example, water or organic solvents.

Individual or a plurality of further elements can be present as promoters in the catalyst. Examples of promoters are metals of transition groups IB, VIB and/or VIII of the Periodic Table, e.g. chromium, iron, molybdenum, nickel, copper, etc.

The activation of the catalysts by leaching, of the soluble component (typically aluminum) can be carried out either in the reactor itself or before introduction into the reactor. The preactivated catalysts are air sensitive and pyrophoric and are therefore generally stored and handled under a medium such as water, an organic solvent or a substance which is present in the reaction according to the invention (solvent, starting material, product) or embedded in an organic compound which is solid at room temperature.

According to the invention, preference is given to using a skeletal cobalt catalyst which has been obtained from a Co/Al alloy by leaching with aqueous alkali metal hydroxide solution, e.g. sodium hydroxide, and subsequent washing with water and preferably comprises at least one of the elements Fe, Ni, Cr as promoters.

Such catalysts typically comprise cobalt together with 1-30% by weight of Al, particularly preferably 2-12% by weight of Al, very particularly preferably 3-6% by weight of Al, 0-10% by weight of Cr, particularly preferably 0.1-7% by weight of Cr, very particularly preferably 0.5-5% by weight of Cr, in particular 1.5-3.5% by weight of Cr, 0-10% by weight of Fe, particularly preferably 0.1-3% by weight of Fe, very particularly preferably 0.2-1% by weight of Fe, and/or 0-10% by weight of Ni, particularly preferably 0.1-7% by weight of Ni, very particularly preferably 0.5-5% by weight of Ni, in particular 1-4% by weight of Ni, with the percentages by weight in each case being based on the total weight of the catalyst.

As catalyst in the process of the invention, use can advantageously be made of, for example, a skeletal cobalt catalyst "Raney 2724" from W.R. Grace & Co. This catalyst has the following composition:

Al: 2-6% by weight, Co: >86% by weight, Fe: 0-1% by weight, Ni: 1-4% by weight, Cr: 1.5-3.5% by weight.

It is likewise possible to use a skeletal nickel catalyst which has been obtained from an Ni/Al alloy by leaching with aqueous alkali metal hydroxide solution, e.g. sodium hydroxide, and subsequent washing with water and preferably comprises at least one of the elements Fe, Cr as promoters for the purposes of the invention.

Such catalysts typically comprise nickel together with 1-30% by weight of Al, particularly preferably 2-20% by weight of Al, very particularly preferably 5-14% by weight of Al, 0-10% by weight of Cr, particularly preferably 0.1-7% by weight of Cr, very particularly preferably 1-4% by weight of Cr, and/or 0-10% by weight of Fe, particularly preferably 0.1-7% by weight of Fe, very particularly preferably 1-4% by weight of Fe, with the percentages by weight in each case being based on the total weight of the catalyst.

As catalyst in the process of the invention, use can advantageously be made of, for example, a skeletal nickel catalyst A 4000 from Johnson Matthey.

This catalyst has the following composition

Al: <14% by weight, Ni: >80% by weight, Fe: 1-4% by weight, Cr: 1-4% by weight.

In the case of decreasing activity and/or selectivity of the catalysts, they can be regenerated by methods known to those skilled in the art, as disclosed, for example, in WO 99/33561 and the documents cited therein.

The regeneration of the catalyst can be carried out in the actual reactor (in situ) or on the catalyst which has been removed from the reactor (ex situ). In the case of fixed-bed processes, regeneration is preferably carried out in situ; in the case of suspension processes, part of the catalyst is preferably taken continuously or discontinuously from the reactor, regenerated ex situ and returned.

The temperatures at which the process of the invention is carried out are in the range from 40 to 150° C., preferably from 70 to 140° C.

The pressure prevailing in the hydrogenation is generally in the range from 5 to 300 bar, preferably from 30 to 250 bar, particularly preferably from 70 to 160 bar.

In a preferred embodiment, the amino nitrile mixture is fed to the hydrogenation at a rate which is not greater than the rate at which the amino nitrile mixture reacts with hydrogen in the hydrogenation.

The feed rate is preferably set so that effectively quantitative conversion is achieved. This is influenced by temperature, pressure, type of mixture, amount and type of catalyst, the reaction medium, quality of mixing of the content of the reactor, residence time, etc.

The optimal operating conditions can differ significantly in the hydrogenation of individual amino nitriles. In the hydrogenation according to the invention of an amino nitrile mixture, however, the operating conditions to be set differ only slightly as a function of the composition and can therefore be optimized more easily. Thus, only a small degree of flexibility of the machines and apparatuses used, as is normally provided by standard commercial equipment (e.g. throughput of pumps, operating temperature of heat exchangers, pressure rating of the apparatuses, etc), is required.

If a solvent is used in the process of the invention, the solvent can firstly be mixed completely with the amino nitrile mixture. The solution obtained, which can, if appropriate, also comprise water and further additives, is subsequently fed into the reaction vessel comprising the catalyst. If appropriate, for example in the case of semibatch processes, part of the solvent can be initially placed together with the catalyst in the reaction vessel, whereupon the solution is metered in. In the case of continuous processes, part of the solvent can also be introduced into the reaction vessel separately from the solution comprising the amino nitrile mixture, the solvent and, if appropriate, water. Since an AAN/IDAN mixture is used, completely separate introduction of the solvent is also conceivable.

The process of the invention for preparing ethylene amines by hydrogenation of amino nitrile mixtures can be carried out continuously, semicontinuously or batchwise in the fixed-bed, fluidized-bed or suspension mode in customary reaction vessels which are suitable for catalysis. Reaction vessels in which contacting of the amino nitrile mixture and the catalyst with the gaseous hydrogen under pressure is possible are suitable for carrying out the hydrogenation.

The hydrogenation in the suspension mode can be carried out in a stirred reactor, jet loop reactor, jet nozzle reactor, bubble column reactor or in a cascade of identical or different reactors of these types. In the case of hydrogenation over a fixed-bed catalyst, tube reactors but also shell-and-tube reactors are conceivable.

In the case of a fixed-bed catalyst, the amino nitrile mixture is conveyed through the catalyst bed in an upward or downward direction. However, the suspension mode is preferably used in semibatch and preferably continuous operation.

The hydrogenation of the nitrile groups takes place with liberation of heat which generally has to be removed. Heat removal can be effected by means of built-in heat-exchange surfaces, cooling jackets or external heat exchangers in a circuit around the reactor. The hydrogenation reactor or a hydrogenation reactor cascade can be operated in a single pass. As an alternative, a recycle mode of operation in which part of the output from the reactor is recirculated to the reactor inlet, preferably without prior work-up of the recycle stream, is also possible. This enables optimum dilution of the reaction solution to be achieved. In particular, the recycle stream can be cooled in a simple and inexpensive manner by means of an external heat exchanger and the heat of reaction can thus be removed. The reactor can also be operated adiabatically, with the increase in the temperature of the reaction solution being able to be limited by means of the cooled recycle stream. Since the reactor itself then does not have to be cooled, a simple and inexpensive construction is possible. An alternative is a cooled shell-and-tube reactor (only in the case of a fixed bed). A combination of the two modes of operation is also conceivable. Here, preference is given to arranging a fixed-bed reactor downstream of a suspension reactor.

The process of the invention gives an ethylene amine mixture comprising EDA and DETA as main component and further ethylene amines (e.g. piperazine) as secondary components. The ratio of the starting materials MN and IDAN is in principle reflected after the hydrogenation in the corresponding products EDA and DETA. Depending on the hydrogenation conditions, further DETA can be formed from AAN. The proportion of DETA in the resulting amine mixture, which comprises EDA as main constituent, can increase by 1-10% by weight as a result.

After the hydrogenation, the product obtained (ethylene amine mixture) can be purified further if appropriate, for example by separating off any solvent used, water and/or the catalyst by methods known to those skilled in the art. In particular, the two main products (EDA and DETA) can be isolated together or individually from the ethylene amine mixture by methods known to those skilled in the art. If the two main products are isolated together, for example by distillation, they can subsequently be separated into the two individual products. Pure EDA and pure DETA are thus ultimately obtained. Other impurities, by-products or further ethylene amines can likewise be separated off from the ethylene amine mixture by methods known to those skilled in the art.

In a preferred embodiment, the process of the invention is carried out using tetrahydrofuran or methanol as solvent. The temperature in the hydrogenation is preferably from 80 to 140° C., and the pressure is preferably from 40 to 160 bar. The hydrogenation is preferably carried out in the absence of ammonia.

A high space velocity over the catalyst, which is a measure of the activity of the catalyst used, is achieved by means of the process of the invention. The space velocity over the catalyst is preferably from 0.3 to 20 mol of nitrile (corresponds to ~0.2 g to 12 g of AAN/g of cat), preferably from 1 to 10 mol of nitrile (~0.6 g-6 g), per gram of catalyst per hour. The higher the space velocity over the catalyst, the higher the space-time yield of ethylene amines can be.

The following examples illustrate the process of the invention. The proportions are given in % by weight, unless indicated otherwise. An internal standard, diethylene glycol dimethyl ether (DEGDME), conveyed with the reaction mixture allows quantification of the product by determination of any volatile decomposition products formed. Quantification is effected by means of gas chromatography (GC), with methanol being added to the samples taken in each case in order to homogenize them.

EXAMPLES

Example 1

Continuous Hydrogenation/30% by Weight of Water 10 g of Cr-doped Raney cobalt are placed in a 270 ml autoclave provided with baffles and a disk stirrer and 50 standard l (standard liters)/h of hydrogen are continuously fed in. A mixture of 30 g/h of AAN, 9 g/h of water in 255 g/h of THF is pumped in continuously at 50 bar. Reaction mixture is discharged continuously via an immersed frit. The reaction temperature is maintained at 120° C. The output is depressurized via a regulating valve. Regular samples are analyzed by means of GC. At no time can MN be detected in the output. The samples show a constant selectivity to EDA of >98% and to DETA of 1%.

6 g/h of the AAN are subsequently replaced by 10 g/h of IDAN for 7 hours, i.e. 24 g/h of MN, 10 g/h of IDAN and 255 g/h of THF are pumped in. Nitrile can no longer be detected in the GC analyses. Here, selectivities to EDA of 66%, to DETA of 30% and to piperazine of 1% are achieved.

For a further 7 hours, 18 g/h of AAN (0.32 mol/h) together with 22.5 g/h of IDAN in 255 g/h of THF including 24 g/h of water are metered in. In this case too, complete conversion of AAN and IDAN occurs. The selectivities of the mixture are 41% of EDA, 51% of DETA and 3% of piperazine.

Comparative Example 1

Continuous Hydrogenation of Crystallized IDAN (Anhydrous)

A) Standard:

10 g of Cr-doped Raney cobalt are placed in a 270 ml autoclave provided with baffles and disk stirrer and 50 standard l/h of hydrogen are continuously fed in. A mixture of 2.9 g/h of IDAN in 60 g/h of THF is pumped in continuously at 180 bar. Reaction mixture is discharged continuously via an immersed frit. The reaction temperature is maintained at 120° C. The output is depressurized via a regulating valve. Regular samples are analyzed by means of GC. No IDAN can be detected during the 140 hour duration of the experiment. The selectivities are 0.5% of EDA, 90% of DETA and 4% of piperazine.

B) Higher Space Velocity Over the Catalyst 6 g of Cr-doped Raney cobalt are placed in a 270 ml autoclave provided with baffles and disk stirrer and 50 standard l/h of hydrogen are continuously fed in. A mixture of 7.5 g/h of IDAN in 140 g/h of THF is pumped in continuously at 170 bar. Reaction mixture is discharged continuously via a cover frit. The reaction temperature is maintained at 120° C. The output is depressurized via a regulating valve. Regular samples are analyzed by means of GC. After 9 hours, 4% of IDAN can be detected. The selectivity to DETA is only 68%. After 24 hours, only 16% of DETA and a conversion of 40% can be detected.

The above examples show that the IDAN present in the amino nitrile mixture can be hydrogenated significantly more quickly in the process of the invention than in processes according to the prior art (comparative examples). Despite the presence of AAN, it is thus possible to hydrogenate 30 times the amount of IDAN per hour compared to the conventional IDAN hydrogenation. Furthermore, it is found that IDAN can also be hydrogenated at much lower pressures. This is advantageous in terms of the equipment used; in addition, the process of the invention can be carried out in the same apparatus as the conventional individual hydrogenation of MN to EDA.

The invention claimed is:

1. A process for preparing an ethylene amine mixture which comprises hydrogenating an amino nitrile mixture comprising at least 30% by weight of aminoacetonitrile (AAN) and at least 5% by weight of iminodiacetonitrile (IDAN) in the presence of a catalyst.

2. The process according to claim 1, wherein the catalyst is Raney catalyst.

3. A process according to claim 1, wherein the catalyst is Raney nickel catalyst or a Raney cobalt catalyst.

4. The process according to claim 1, wherein the hydrogenation is carried out in the presence of water or an organic solvent.

5. The process according to 4, wherein the organic solvent is tetrahydrofuran or methanol.

6. The process according to claim 1, wherein the pressure is from 40 to 160 bar or the temperature is from 80° C. to 140° C.

7. The process according to claim 1, wherein the amino nitrile mixture comprises from 10 to 25% by weight of IDAN.

8. The process according to claim 1, wherein ethylenediamine (EDA) and diethylenetriamine (DETA) and optionally further ethylene amines are isolated from the ethylene amine mixture after the hydrogenation.

9. The process according to claim 1, wherein AAN or IDAN are prepared by reaction of $NH_3$ and formaldehyde cyanohydrin (FACH).

10. The process according to claim 1, wherein the amino nitrile mixture is fed to the hydrogenation at a rate which is not greater than the rate at which the amino nitrile mixture reacts with hydrogen in the hydrogenation.

11. The process according to claim 1, wherein the hydrogenation is carried out without addition of ammonia.

12. The process according to claim 3, wherein the hydrogenation is carried out in the presence of an organic solvent wherein the organic solvent is tetrahydrofuran or methanol.

13. The process according to claim 12, wherein the pressure is from 40 to 160 bar and the temperature is from 80° C. to 140° C.

14. The process according to claim 13, wherein the amino nitrile mixture comprises from 10 to 25% by weight of IDAN.

* * * * *